United States Patent [19]

Braunstein et al.

[11] Patent Number: 5,346,589
[45] Date of Patent: Sep. 13, 1994

[54] CRYSTALLINE CELLULOSE PRODUCTION

[75] Inventors: Edit L. Braunstein, Rochester; Robert L. Dostie, Penfield; Keith H. Germano, Webster; Steve C. Lamb, Victor; Christopher S. Penet, Henrietta; Paul B. Richards, Rochester, all of N.Y.

[73] Assignee: Genencor International, Inc., Rochester, N.Y.

[21] Appl. No.: 937,825

[22] PCT Filed: Feb. 21, 1992

[86] PCT No.: PCT/US92/01387
§ 371 Date: Oct. 20, 1992
§ 102(e) Date: Oct. 20, 1992

[87] PCT Pub. No.: WO92/14760
PCT Pub. Date: Sep. 3, 1992

[51] Int. Cl.$^5$ .............................................. D21C 3/20
[52] U.S. Cl. .................................. 162/72; 435/101; 435/277; 536/56
[58] Field of Search .............. 162/72 B; 435/101, 277; 536/56, 124, 126

[56] References Cited

U.S. PATENT DOCUMENTS

| | | | |
|---|---|---|---|
| 3,141,875 | 7/1964 | Battista et al. | 536/56 |
| 4,028,132 | 6/1977 | Litt et al. | 106/163 |
| 4,427,778 | 1/1984 | Zabriskie | 435/277 |
| 4,645,541 | 2/1987 | DeLong | 127/37 |
| 4,923,565 | 5/1990 | Fuentes et al. | 435/277 |
| 5,175,275 | 12/1992 | Dobashi et al. | 536/56 |

FOREIGN PATENT DOCUMENTS 0165901 12/1980 Japan.

OTHER PUBLICATIONS

Nelson et al., Journal of Applied Polymer Science, vol. 8, pp. 1325–1341; 1964.

Primary Examiner—Michael W. Ball
Assistant Examiner—Nancy T. Krawczyk
Attorney, Agent, or Firm—Margaret A. Horn

[57] ABSTRACT

The present invention relates to new methods for producing cellulose with high crystallinity by enzymatic hydrolysis and to novel cellulosic materials produced by those methods which exhibit a wide variety of DP's. The method is especially useful in producing microcrystalline celluloses.

8 Claims, No Drawings

CRYSTALLINE CELLULOSE PRODUCTION

This is based upon PCT US92/01387, filed on Feb. 21, 1992 which was based upon U.S. patent application Ser. No. 07/660,384 filed on Feb. 21, 1991, now abandoned.

BACKGROUND OF THE INVENTION

1. Field of the Invention

The present invention relates to the preparation of microcrystalline cellulose products (crystallinity of at least 78%) via enzymatic hydrolysis of certain cellulosic materials. The invention further relates to the enzymatic production of said microcrystalline cellulose exhibiting high crystallinity at LOPD.

2. State of the Art

Crystalline cellulose, or MCC, defined as cellulose with a crystallinity of at least 78%, has a wide variety of applications such as tabletting excipient, anti-caking aids, filler, carrier, formation of stable dispersions (alone in co-processed forms with other materials such as CMC, whey protein and so on), source of fiber, etc., for the food, pharmacy, and cosmetic industries.

The current commercially available forms of microcrystalline cellulose (MCC) are produced from a high grade of dissolving pulps and hydrolyzed to LODP of about 200–300 and contain crystallinities as measured by x-ray diffraction of greater than 78%. They are produced, as described by U.S. Pat. No. 2,978,446 to Battista, et al., by subjecting wood pulp containing amorphous and crystalline forms of cellulose to acid hydrolysis at elevated temperature, usually in 2.5 normal hydrochloric acid, on the order of 105° C. or greater, for about 15 minutes to one hour, followed by mechanical disintegration of the cellulose hydrolysate. The process is generally carried out by hydrolyzing a pure grade of wood pulp with hydrochloric acid in order to prevent the formation of undesirable by-products from secondary reactions. The hydrolysis reaction removes amorphous cellulose and reduces the degree of polymerization of the cellulose chain leaving a substantially insoluble material, which is commonly referred to in the art as "level-off degree of polymerization" (LODP) cellulose.

The LODP value is dependent primarily upon the starting cellulosic material and to a lesser extent upon the severity of the hydrolyzing conditions. In general, the LODP of native cellulose fibers is in the range of between about 200–400, whereas that derived from regenerated cellulose lies in the range of from 25 to about 60.

It has been the general view of those knowledgeable about the manufacture and applications of microcrystalline cellulose powder that the only way to achieve the LODP value for a given cellulosic material, with crystallinity above about 78%, was by acid hydrolysis, as described above. This view was based primarily on the belief that only inorganic acids had the requisite reactivity and accessibility to attack the more tightly bound portions of the cellulose structure, and produce LODP cellulose at high crystallinity of 78% or more. It was previously thought that microcrystalline cellulose could not be produced at other than the LODP of the starting material.

In the prior art, although other methods of cellulose degradation, e.g., enzymatic hydrolysis, have been studied and reported such methods have not been considered appropriate for commercial microcrystalline cellulose powder production with LODP because they have not produced crystallinity above 78%.

In U.S. Pat. No. 4,427,778 (Zabriskie), a method using cellulase for making cellulose powder suitable for tabletting was described using a pH of about 4–5 at temperatures around 50° C. DP's were obtained down to about 880 or so, and the percent crystallinity reported never got above about 75%, i.e., never made microcrystalline cellulose and never achieved LODP.

Some difficulties with the acid hydrolysis method are the energy required to boil the acid, the corrosive nature of the acid, the inability to control the reaction and the inability to obtain DP's other than LODP. In addition, a problem with the previous enzymatic method is that crystallinity greater than 75% is never achieved and DP's below about 80 are not seen.

The present invention provides an enzymatic route to producing LODP MCC enzymatical for use as an alternative in the manufacture of various articles.

It is also now possible to produce MCC at greater than 78% crystallinity and greater than LODP.

SUMMARY OF THE INVENTION

It has now been discovered that cellulosic raw materials such as purified wood pulps with starting DP's of about 1100–1300 may be converted to LODP microcrystalline cellulose by the use of endo-cellulose type activities achieving LODP's in the range of 200–300. It is also disclosed that this cellulose hydrolysis treatment yields highly crystalline materials in the order of 78% or higher by x-ray diffraction which is the normal value for crystallinity or commercial MCC produced via acid hydrolysis.

Enzymatic hydrolysis of cellulose to its highly crystalline breakdown product (MCC) in the present invention has advantages over prior art methods such as acid hydrolysis, in that the enzymatic process is less drastic a method of achieving LODP and can be carried out with less extreme pH conditions. In the present invention advantage over previous enzymatic hydrolysis is achieved by the ability of the invention to achieve LODP of cellulose coupled with high crystallinities required for MCC production.

Accordingly, the invention relates to a process for converting a cellulosic material to microcrystalline cellulose comprising subjecting a cellulosic material to hydrolysis using an enzyme having endo-cellulosic activity at a temperature of about 35°–75° C. and at a pH from about 2.0 to 4.0 for a time sufficient to form a cellulose having a crystallinity of at least about 78%. The invention also relates to novel compositions comprising cellulose with crystallinity above about 78% with a DP above the LODP of the cellulose preferably up to a DP of about 800 or so.

The process herein not only produces compositions not heretofore achievable with prior processes but produces crystalline cellulose without employing extended temperature reaction conditions and therefore production may be possible at reduced capital and operating costs. Unlike previous enzymatic processes, a higher degree of crystallinity can be achieved, as well as degradation down to LODP.

DETAILED DESCRIPTION OF THE INVENTION

Various grades and forms of cellulosic materials may be used as the starting material in the process of the present invention without the occurrence of undesired side reactions because of the specificity of the enzyme. Such materials include natural sources of cellulose or products derived from natural sources of cellulose. Results can be obtained using readily available cellulosic raw materials, such as a dissolving-grade of wood pulp, muslin cloth, exploded wood pulp and cotton linters. Concerning these raw materials, the dissolving-grade of wood pulp is a highly refined material used in the commercial preparation of microcrystalline cellulose and is the raw material of preference for this invention. Muslin cloth is similar to cotton trim ends, which is a waste material in the manufacture of cotton fabrics. Exploded wood pulp is a cellulose material which has undergone treatment with steam at high temperature and pressure followed by an explosive decompression step. This latter treatment of exploded wood pulp has been reported to remove hemicellulose, expose lignin and to increase the reactive surface area of the material. It is beneficial to further subject the exploded wood pulp to an alkali-alcohol extraction to remove lignin.

Especially preferred as cellulosic material in this invention is wetlap pulp, i.e., undried pulp, pulp slurry or other hydrated plant cellulosic material which has never been dried at any point in the pulp processing, obtained from normal pulp or plant processing methods in such a way that dehydration or moisture removal from the material is minimized and high cellulose content achieved. The wet ground material preparation in this invention prior to drying can be obtained from normal pulp or plant processing methods. An example is Sulfatate H-J pulp obtained as wetlap from southern hardwoods by the prehydrolyzed sulfate process of ITT Rayonier.

Enzymes for use in the method of the invention have endo-cellulase activity and are available from various native microbial and, more recently, recombinant microbial sources. These include commercial preparation of cellulase (a combination of several different enzymes having both endo- and exo-cellulase activity) or cellulase which have been enriched with particular components having endo-cellulase activity or modified to reduce or remove a particular component having exo-cellulase activity. Endo-cellulase activity selectively removes the amorphous regions of the cellulose. Exo-cellulase activity acts to remove crystalline portions and is, therefore, less desirable. A rich source of cellulase is from the organism Trichoderma viride and several commercial preparations are available including those with enriched endo-cellulase activity. The preferred concentration of enzyme would be from about 100 ppm to about 5000 ppm of enzyme where the cellulosic material is present at a concentration of from about 0.25 g/l to 75 g/l. Preferred is Cytolase 123 available from Genencor International, Inc. where the product is added in about 0.5 g/l to about 4.0 g/l. Even more preferred is a cellulase material that is CBHI and/or CBHII deleted. One skilled in the art would realize that various enzymes have different specific activities and as such, differing amounts are necessary to achieve the same results. However, determining the precise amount of enzyme is well within the scope of the art in view of the teachings of the invention.

Enzymatic hydrolysis of the invention is carried out in an aqueous solution, and at a temperature of from about 35°–75° C., preferably between 40°–60° C. and most preferably between about 50° C. to about 60° C. The hydrolysis is critically carried out at a pH of from about 2–4 and preferably from about pH 2.5–3.5, and most preferably from about pH 2.5–3.0.

The exact time for the hydrolysis reaction will vary depending on the nature of the starting material, the pH and the amount and specific activity of the enzyme, but in general the desired result can be achieved within 24 hours or less. Various processing conditions, including but not limited to time, temperature, pH, pulp type and enzyme concentration will produce MCC. These conditions can also produce a range of products such that a crystalline cellulose having 78% crystallinity or more is produced with a DP ranging from the native starting DP of the cellulosic material down to the LODP. After hydrolysis, mechanical disintegration (e.g., by shearing) of the crystalline cellulosic material effects a variety of achievable particle sizes. This is especially useful in the production of microcrystalline cellulose.

After hydrolysis and shearing, another critical processing step necessary for MCC production, as described by Battista, is the drying of the cellulose, either by conventional techniques or subjecting it to spray drying or according to other drying methods well known in the art of formulated accordingly. The final product can be used in a wide variety of products including tablet making, adhesive binders, dry lubricants, emulsion stabilizers, ink permutates, mold compositions, pesticide carriers, rubber additives, wood floors, pet food, baby products, starch products, mouth feel additive in suspensions, paints, cosmetics, packaging, dairy products, salad dressings, baked goods and the like.

EXAMPLE 1

Hydrolysis reactions were conducted in 1 liter, temperature controlled water baths utilizing "Lightnin" type agitators equipped with Rushton turbine blades. Agitation was conducted at 500 rpms for the extent of the reaction.

For this example 100 gms of wetlap sulfatate HJ pulp was added to 900 gms of pH 2.9 buffer prepared in HCL. The reaction temperature was controlled at 65° C. and enzyme levels (Cytolase 123) tested at 0.5 g/l and 4.0 g/l. The reaction was carried out for 24 and 48 hours at which time samples were removed from the reaction vessel and denatured via vacuum filtration. Samples were then washed and subsequently denatured, as described, through 5 cycles, utilizing copious amounts of water until such time that the pH of the wash reached 7.0. Samples were then freeze dried and DP's measured. The DP results are listed below:

| Enzyme Level | 24 Hr. | 48 Hr. |
| --- | --- | --- |
| 0.5 g/l | 345 | 321 |
| 4.0 g/l | 275 | 254 |

EXAMPLE 2

A statistically designed, central composite study was initiated to fully optimize the conditions to obtain the lowest DP with economically feasible variables. The design centered around pH, temperature, enzyme level and utilized a cellulase preparation deleted of one component having exo-cellulase activity specifically cellobiohydrolase I. The experiments and reactions were carried out as described in Example 1. The ranges studied in this test were as follows:

pH levels range from 2.8–6.2;

Temperature levels ranging from 46°–63.5° C.;
Enzyme conc S levels ranging from 0–2.5 g/l.

A DP of 296 was obtained (without shear) utilizing these conditions: pH=3.5, temp=55° C., enzyme=2 g/l, time 24 hours, obtained yield of 90%.

EXAMPLE 3

Enzyme preparation of cellulase with CBH I and II removed (16 g/l protein) was utilized in this example. Again, wetlap sulfatate HJ was used and experimental conditions were as previously described. Enzyme was tested at 8, 10 and 12 g/l; temperature was 55° C.; pH 3.0 and all reactions carried out for 24 hours. A finished DP of 353 was achieved.

EXAMPLE 4

Example 3 was repeated utilizing an enriched preparation of CBH I and II deleted enzyme product at 133 g/l of protein. Reaction conditions were identical and enzyme levels were tested at 2 and 3 g/l respectively.

Also incorporated into this example was sample of the sulfatate HJ pulp which had been dried through the normal drying operations at the pulp mill. Results are listed below:

| Pulp | Enz Conc | DP/24 Hr |
|---|---|---|
| dry HJ | 2 g/l | 661 |
| wet HJ | 2 g/l | 402 |
| wet HJ | 3 g/l | 292 |

EXAMPLE 5

A series of statistically designed experiments were run to screen a variety of pulps (both hard and softwoods) obtained in their normal commercial forms prepared as dry sheets of pulp received from the mills. Multiple variables were screened and included pH, temperature, enzyme level, time of hydrolysis, and one experiment utilizing various enzyme preparations. Results were analyzed by DP measurements. Hydrolysis reactions were carried out as described previously utilizing the Rushton-Turbine blades at 500 rpms. The data shown below summarizes the results of these screening experiments.

| PULP TYPE | pH | TEMP. | ENZ. LEVEL | RXN. TIME | DP |
|---|---|---|---|---|---|
| Pontiac Maple | 4.0 | 40° C. | 4.0 g/l | 24 hr. | 694 |
| St. Anne Ultra | 4.0 | 40 | 4.0 | 24 hr. | 701 |
| Tembec | 4.0 | 60 | 4.0 | 24 | 870 |
| Temphite | 4.0 | 60 | 4.0 | 24 | 744 |
| St. Anne Reg. | 4.0 | 60 | 4.0 | 24 | 727 |
| HVX | 4.0 | 60 | 4.0 | 24 | 623 |
| Solka Floc40 | 4.0 | 60 | 4.0 | 24 | 748 |

-continued

| PULP TYPE | pH | TEMP. | ENZ. LEVEL | RXN. TIME | DP |
|---|---|---|---|---|---|
| Solka Floc200 | 4.0 | 60 | 4.0 | 24 | 670 |
| NBH | 4.0 | 60 | 4.0 | 24 | 744 |
| Poplar | 4.0 | 60 | 4.0 | 24 | 727 |
| Aspen | 4.0 | 60 | 4.0 | 24 | 623 |
| St. Croix | 4.0 | 60 | 4.0 | 24 | 748 |
| Puget Alpha | 4.0 | 60 | 4.0 | 24 | 670 |
| Canfor 1072 | 4.0 | 60 | 4.0 | 24 | |
| Sulfatate HJ | 4.0 | 60 | 4.0 | 24 | 838 |
| Eucalyptus | 4.0 | 60 | 4.0 | 24 | 656 |
| Sulfatate HJ | 2.35 | 55 | 2.0 | 24 | 510 |
| Repap | 4.0 | 60 | 4.0 | 24 | 565 |
| Ga. Pacific | 4.0 | 60 | 4.0 | 24 | 818 |
| Sulfatate HJ Cytolase 123 | 2.6 | 65 | 4.0 | 24 | 521 |
| CBHl deleted | 2.6 | 65 | 4.0 | 24 | 569 |
| Mileszyme | 2.6 | 65 | 4.0 | 24 | 626 |
| Multifect | 2.6 | 65 | 4.0 | 24 | 598 |
| Celluzyme | 2.6 | 65 | 4.0 | 24 | 803 |

We claim:

1. A process for converting a cellulosic material to a crystalline cellulose material, the process comprising:
   a) selecting as a starting material, a never dried cellulosic material; and
   b) subjecting the never dried material to enzymatic hydrolysis using a cellulase enzyme at a temperature of from about 35°–75° C., and at a pH from about 2.0 to 4.0, for a time sufficient to form crystalline cellulose having a degree of polymerization (DP) from about 800 down to the level-off degree of polymerization (LODP) of the starting material.

2. A process of claim 1 wherein the starting material is wetlap pulp.

3. A process of claim 1 wherein the cellulase is a Trichoderma cellulase.

4. A process of claim 1 wherein the cellulase is enriched in endo-cellulase activity.

5. A process of claim 1 wherein the cellulase is reduced for exo-cellulase activity.

6. A process of claim 1 wherein the cellulase is present at an amount from about 0.5 g/L to about 4.0 g/L.

7. A process for converting a cellulosic material to a crystalline cellulose material, the process comprising:
   a) selecting a never dried cellulosic material; and
   b) subjecting the never dried cellulosic material to enzymatic hydrolysis at a temperature from about 50°–60° C., and at a pH from about 2.5 to 3.5, for a period sufficient to form crystalline cellulose having a degree of polymerization (DP) from about 700 down to the level-off degree of polymerization (LODP) of the never dried cellulosic material.

8. An improved crystalline cellulose having a degree of polymerization (DP) from about 200–700, the improvement comprising producing the crystalline cellulase by enzymatic hydrolysis of a never dried cellulose starting material.

* * * * *